(12) United States Patent
Chu (10) Patent No.: US 8,491,458 B2
(45) Date of Patent: Jul. 23, 2013

(54) MEDICAL DEVICE TO DELIVER PELVIC FLOOR IMPLANT

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 483 days.

(21) Appl. No.: 12/623,867

(22) Filed: Nov. 23, 2009

(65) Prior Publication Data

US 2010/0145140 A1 Jun. 10, 2010

Related U.S. Application Data

(60) Provisional application No. 61/120,196, filed on Dec. 5, 2008.

(51) Int. Cl.
*A61F 2/04* (2006.01)

(52) U.S. Cl.
USPC .................................. 600/37; 630/29; 630/30

(58) Field of Classification Search
USPC ................................. 600/37, 29–30
See application file for complete search history.

(56) References Cited

U.S. PATENT DOCUMENTS

| 7,686,506 | B2 * | 3/2010 | Babkes et al. | 374/158 |
| 8,187,247 | B2 * | 5/2012 | Lornell | 604/392 |
| 2002/0151909 | A1 | 10/2002 | Gellman et al. | |
| 2004/0267088 | A1 * | 12/2004 | Kammerer | 600/37 |
| 2006/0195007 | A1 | 8/2006 | Anderson et al. | |
| 2007/0202542 | A1 * | 8/2007 | Babu et al. | 435/7.1 |
| 2008/0287732 | A1 * | 11/2008 | Kuntz | 600/37 |
| 2009/0137944 | A1 * | 5/2009 | Haarala et al. | 604/44 |
| 2009/0171140 | A1 | 7/2009 | Chu | |

FOREIGN PATENT DOCUMENTS

| WO | 2007/059306 A1 | 5/2007 |
| WO | 2010/065592 A1 | 6/2010 |

OTHER PUBLICATIONS

International Search Report and Written Opinion for PCT Application No. PCT/US2009/066344, mailed on Feb. 4, 2010, 16 pages.
International Preliminary Report on Patentability for International Patent Application No. PCT/US2009/066344, mailed on Jun. 16, 2011, 8 pages.

* cited by examiner

*Primary Examiner* — Charles A Marmor, II
*Assistant Examiner* — Thaddeus Cox (57) ABSTRACT

An apparatus includes a support member, a strap extending from the support member, and a sleeve releasably disposed over at least a portion of the strap. The support member is configured to support a portion of a body of a patient. The strap is configured to be inserted through at least a portion of a tissue of the patient. The sleeve is releasably coupled to the strap by a releasable joint. The sleeve is configured to be removed from the strap when at least a portion of the strap is disposed within the tissue of the patient.

28 Claims, 9 Drawing Sheets

MEDICAL DEVICE TO DELIVER PELVIC FLOOR IMPLANT

CROSS-REFERENCE TO RELATED APPLICATIONS

This application claims priority to U.S. Provisional Patent Application Ser. No. 61/120,196, entitled "Method and Device to Deliver Pelvic Floor Implant," filed Dec. 5, 2008, the disclosure of which is hereby incorporated by reference in its entirety.

BACKGROUND

The invention relates generally to medical devices and more particularly to implants and methods for delivering implants within a pelvic region of a patient to treat various pelvic dysfunctions.

A variety of medical procedures are performed to treat various female pelvic dysfunctions, including procedures to treat urinary incontinence, and to correct various prolapse conditions such as uterine prolapse, cystoceles, rectoceles, and vaginal vault prolapse.

Women often experience vaginal prolapse due to age or other factors. For example, women may experience a cystocele, a rectocele and/or a hysterocele. A cystocele occurs when the bladder bulges into the vagina, and a rectocele occurs when the rectum bulges into the vagina. A hysterocele occurs when the uterus descends into the vagina. An enterocele (small bowel prolapse) can also occur, when the small bowel pushes through the upper wall of the vagina. It is relatively common for a hysterocele and cystocele or hysterocele and rectocele, or other combinations thereof to occur at the same time. It is also common for different types of prolapse to occur in relatively quick succession.

Treatment has included suturing procedures or the use of implants for support or suspension. A hysterocele is often treated with a hysterectomy followed by a vaginal vault suspension. Various devices and procedures are used to deliver and secure pelvic implants within a variety of different anatomical structures within a pelvic region. Implants can be delivered to a pelvic region through one or more vaginal incisions, and/or through exterior incisions in the patient.

Depending on the particular condition to be treated and the implant used, pelvic floor repair can require various fixation locations within a pelvic region. For example, an implant can be secured using a number of fixation points. Sutures are often used to bridge, anchor and/or suspend the implant in place. Sutures may not provide enough surface area for tissue in-growth, and may require knotting in order to be secured. Implants formed with mesh material can provide for tissue in-growth and the width of the mesh can help prevent tissue cutting. An implant can also have roughened or tanged edges to grip surrounding tissue and hold the mesh implant in place until tissue in-growth occurs. Delivery of some implants includes the use of a sleeve to cover some or all of an implant to protect the implant from damage during delivery and to prevent premature engagement of the implant (including the roughened or tanged edges) to surrounding tissue.

Various complications can occur during a procedure to deliver and secure a pelvic implant due to, for example, space constraints for performing the implantation procedure. Often, implants can become damaged during delivery due to the type of delivery device and/or the type of implant, or due to excessive handling of the implant during the implant procedure. Thus, it would be desirable to provide improved pelvic implants that are easier to manufacture and implant within a body of a patient and delivery processes associated with such implants to help prevent damage to the implant during implantation.

SUMMARY

In some embodiments, an apparatus includes a support member, a strap extending from the support member, and a sleeve releasably disposed over at least a portion of the strap. The support member is configured to support a portion of a body of a patient. The strap is configured to be inserted into a tissue of the patient. The sleeve is releasably coupled to the strap by a releasable joint. The sleeve is configured to be removed from the strap when at least a portion of the strap is disposed within the tissue of the patient.

DETAILED DESCRIPTION

In some embodiments, an apparatus includes a support member, a strap extending from the support member, and a sleeve releasably disposed over at least a portion of the strap. The support member is configured to support a portion of a body of a patient. The strap is configured to be inserted through at least a portion of a tissue of the patient. The sleeve is releasably coupled to the strap by a releasable joint. The sleeve is configured to be removed from the strap when at least a portion of the strap is disposed within the tissue of the patient.

In some embodiments, an apparatus includes a sleeve releasably coupled to a strap of an implant by a releasable joint, a dilator coupled to the sleeve, and a dart coupled to the dilator. The dart is configured to pierce a tissue of the patient when the dart is inserted through the tissue. The dilator is configured to dilate the tissue of a patient when the dilator is inserted through the tissue. The releasable joint is configured to brake and/or release and the sleeve is configured to be removed from the strap of the implant when a force is applied to the strap at a position along the strap and the sleeve is pulled in a direction away from the strap.

In some embodiments, a method includes inserting a pelvic implant into a body of a patient through a vaginal incision. The pelvic implant includes a support portion, a strap extending from the support portion, and a sleeve disposed over at least a portion of the strap. After inserting the pelvic implant, the strap and the sleeve are pulled at least partially through a pelvic tissue such that the strap is disposed at least partially within the pelvic tissue. A releasable joint on the sleeve is then broken and the sleeve is removed from the strap.

An implant, according to an embodiment, can include one or more tanged portions. The terms "tanged" or "tangs" as used herein mean roughened or jagged edges or areas, such as can result from cutting a woven or knit mesh material. The tanged portion can be used, for example, to anchor or secure the implant to tissue. An implant, according to an embodiment, can be implanted, for example, through a vaginal incision. A procedure to deploy the implant can include a single vaginal incision, such as an anterior vaginal incision.

Implants can be delivered to a pelvic region of a patient using a variety of different delivery devices, only some examples of which are described herein. Various delivery aids are also described, some of which can be included as part of an implant (e.g., provided to a physician assembled) and some of which can be coupled to or associated with an implant just prior to implantation. Such delivery aids are typically removed after placing one or more straps of an implant at a desired tissue securement location, leaving the strap to engage the tissue and support the support portion of the implant. For example, a sleeve or dilator assembly can be used to lead an implant or a strap of an implant through a tissue in an intracorporeal location (i.e., within the patient's body), such as the sacrospinous ligament or arcus tendineus fasciae pelvis. In other embodiments, a sleeve or dilator assembly can be used to lead an implant or a strap of an implant through a tissue and to an extracorporeal location (outside the patient's body), such as through an obturator membrane or muscle and out through an exterior incision in the patient.

Figure 1:
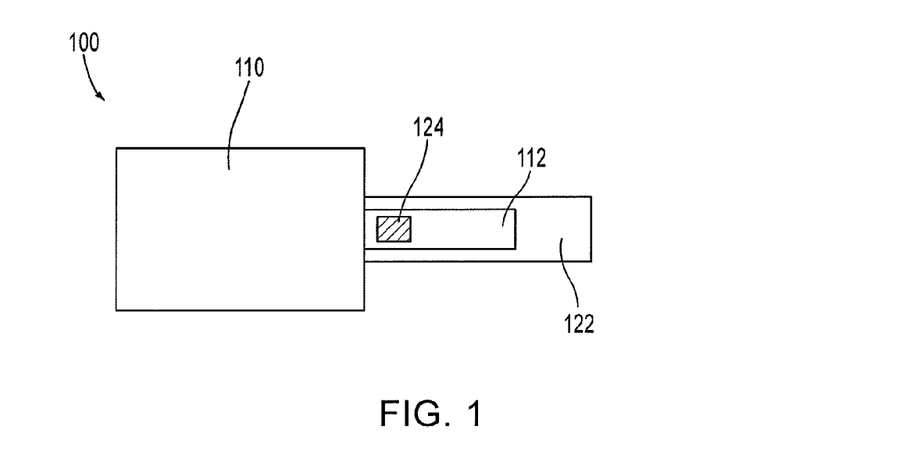
FIGS. 1 and 2 are schematic illustrations of an implant in a first configuration and a second configuration respectively, according to an embodiment.
Figure 2:
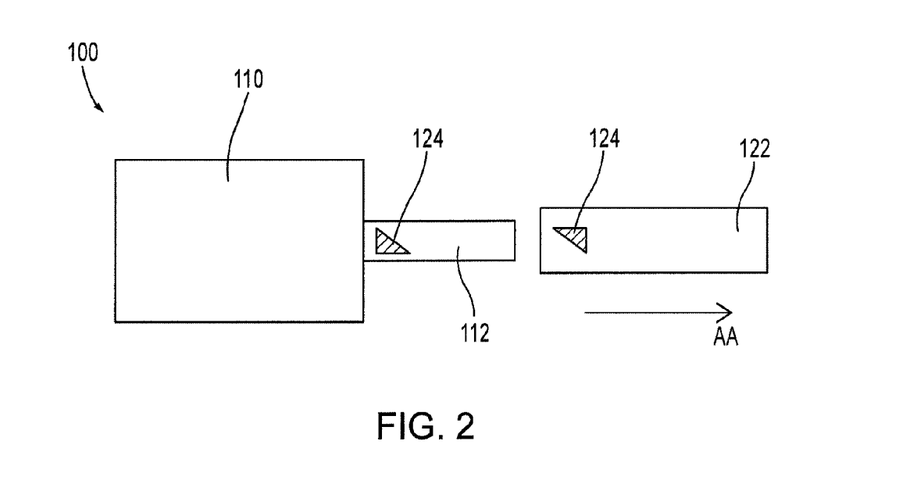

FIGS. 1 and 2 are schematic illustrations of an implant 100 in a first configuration and a second configuration, respectively, according to an embodiment. Implant 100 includes a support member 110, a strap 112, and a sleeve 122 configured to be releasably coupled to the strap 112.

The support member 110 is configured to be placed within a body of a patient and is configured to support a portion of the body. For example, the support member 110 can be similar to the grafts disclosed in U.S. Patent Application No. 61/017, 257 entitled "Apparatus and Method for Uterine Preservation," filed on Dec. 28, 2007, which is hereby incorporated by reference in its entirety. For example, the support member 110 can be a variety of different shapes, sizes and configurations depending on the intended use for the particular implant. In some embodiments, the support member 110 can be substantially rectangular, square, oval, or elliptical. The support member 110 can be shaped and sized to support a bladder (e.g., to treat a cystocele) and/or a bladder neck and/or support a uterus (e.g., to treat a hysterocele) and/or to support a rectum (e.g. to treat a rectocele).

The support member 110 can be formed with a mesh material to allow tissue in-growth to the implant 100 after implantation. For example, some or all of the support member 110 can be formed with a mesh material as described in U.S. Patent Pub. 2005/0038452 A1 to Chu, the disclosure of which is hereby incorporated by reference in its entirety. In some embodiments, some or all of the support member 110 can be formed with the Advantage® Mesh or the Polyform™ Synthetic Mesh material each provided by Boston Scientific Corporation ("BSC").

The strap 112 of the implant 100 is coupled to and extends from the support member 110 of the implant 100. The strap 112 is configured to support the support member 110 of the implant 100 when the strap 112 is inserted into a tissue of the patient.

In some embodiments, the strap 112 is formed with the same material as the support member. In other embodiments, the strap is formed with a different material than the support member. For example, the support member can be formed with a first biocompatible material and the strap can be formed with a second biocompatible material different than the first biocompatible material. In another example, the support member is formed with a biological material, and the strap can be formed with a synthetic material. The strap and support member can also have a different weave, pitch, texture, color, and/or pattern from each other. In some embodiments, the strap 112 is, for example, a polymer.

In some embodiments, the strap 112 is formed monolithically with the support member 110. In other embodiments, the strap is a separate component coupled to the support member. For example, the strap and the support member can be coupled in an abutting relationship, an overlapping relationship, or can be bridged. The strap can be coupled to the support member by, for example, heat bonding, gluing, using fasteners, and/or sewing. In some embodiments, the strap includes a heat seal along its length or a portion of its length to help prevent or reduce stretching of the strap.

In some embodiments the support member 110 and/or the strap 112 include one or more tanged portions (as described above). The tangs allow the implant 100 to be anchored within tissue, such as pelvic tissue, without the use of additional anchoring mechanisms or sutures. In some embodiments, an implant 100 includes tangs on an edge along an entire length of the implant 100. In other embodiments, the implant 100 includes tangs covering substantially all of an exterior surface of the implant. In some embodiments, tangs are only on the strap 112 of the implant 100. For example, in some embodiments the strap 112 includes a tanged portion to engage and/or help secure the implant to pelvic tissue. Pelvic tissue can include, for example, ligaments (such as a sacrospinous ligament), muscle (such as an obturator internus muscle or an obturator externus muscle), fascia, or any other structure or tissue within a pelvic region of a patient.

As with the support member 110, the strap 112 can have a variety of different configurations and/or different sizes (e.g. lengths, widths), depending on the intended use for the particular implant and the intended implantation site for the strap 112 within the pelvic region. For example, the length of the strap 112 can depend on the particular tissue (e.g., ligament, muscle) that the strap 112 is intended to be secured to, such that trimming of the strap 112 during or after placement can be reduced or eliminated. For example, a strap can have a length such that the strap can be placed through, and/or secured to, tissue, such as a sacrospinous ligament, but is not long enough to return back through a vaginal insertion point. In some embodiments, the strap 112 has a length such that it extends from a pelvic region through an exterior incision of the patient. In other embodiments, the strap has a length just sufficient to be secured to a target tissue site. This allows the implant to be formed with less material. The use of a strap having a length configured for the particular use can thus eliminate the need for trimming and also reduce the costs to manufacture the implant. Such embodiments of a strap can also help prevent strap stretch that can occur during insertion of the implant due to pulling on a longer length strap.

While the implant 100 is shown in FIG. 1 having a single strap 112, in other embodiments, the implant can have any number of straps depending on the particular intended use for the implant. For example, the implant can have between one and twenty straps. In some embodiments, one or more straps extend from the support member at an angle. Such an angle of a strap can vary in different embodiments, for example, between 20 and 160 degrees from a centerline of the support member.

The sleeve 122 of the implant 100 can be made of any suitable material, such as, for example, polymer, and is releasably coupled to the strap 112 by a releasable joint 124. Because a releasable joint is used to couple the sleeve 122 to the strap 112, the sleeve 122 is uncoupled from the strap 112 without using a tool to sever a portion of the sleeve 122 and/or strap 112. For example, the releasable joint 124 can be configured to break and/or release when a predetermined force is exerted on the releasable joint 124. In some embodiments, the releasable joint 124 is frangible and configured to break and/or release when a force is exerted on the releasable joint. For example, in some embodiments the releasable joint 124 is configured to break and/or release when a force of about 4 lbf to 6 lbf is exerted on the releasable joint 124. In other embodiments, the releasable joint is configured to break and/or release when a force greater than 6 lbf is exerted on the releasable joint. In still other embodiments, the releasable joint is configured to break and/or release when a force less than 6 lbf is exerted on the releasable joint.

The releasable joint 124 can include a heat weld, glue, an interference fit, a controllably tearable portion, and/or mechanical engagements such as fasteners. For example, in some embodiments, a polymer sleeve is heat welded to a polymer strap. In other embodiments, the sleeve is coupled to the strap by multiple releasable joints, such as, for example, multiple heat welds. This affords greater flexibility to the sleeve and can minimize damage to the strap when the releasable joints are broken. In some embodiments, the sleeve 122 defines a lumen that is configured to receive at least a portion of the strap 112.

The sleeve 122 can be used during the insertion of the implant into a pelvic region to prevent the strap 112 from prematurely engaging tissue during the delivery procedure. For example, if the strap 112 includes a tanged portion, the sleeve 122 can prevent the tangs from engaging tissue as the implant is being delivered into the pelvic region. Conversely, when no sleeve is coupled to the strap 112, the tangs can engage the surrounding tissue making it difficult to smoothly slide and/or adjust the strap 112. The sleeve 122 can also help in adjusting the tension of a strap 112, for example, to relieve strap tension. The sleeve 122 can also protect the strap 112 from damage during delivery.

The sleeve 122 can be transparent, semi-transparent, colored, non-colored, or a combination thereof. The sleeve 122 can be, for example, tapered, flat, and/or tubular. A sleeve 122 can be formed for example, with a clear, thin, flexible biocompatible polymer, and be configured to allow the user to examine or view the implant 100 (e.g., straps) disposed within the sleeve 122. After the strap 112 is positioned at a desired location within the pelvic region, the sleeve 122 can be removed from the strap 112, as described in more detail below.

In one embodiment, the sleeve 122 extends beyond the strap 112. The sleeve 122 can thus be used to provide an extension to the strap 112 to help in the insertion process. The sleeve 122 can also help maintain the cleanliness of the strap 112 during insertion as a portion of the strap 112 that will be secured within the pelvic region will be protected within the sleeve 122. This can also reduce friction between the strap 112 and an interior surface of the sleeve 122 (due to reduced surface area contact) allowing easier, removal of the sleeve 122.

The implant 100 includes a first configuration (FIG. 1) and a second configuration (FIG. 2). The implant 100 is in the first configuration when the sleeve 122 is coupled to the strap 112 by the releasable joint 124. The implant 100 is moved from the first configuration to the second configuration, by pulling the sleeve 122 with respect to the strap 112 in the direction shown by the arrow AA in FIG. 2 while holding the strap 112 in place. When the sleeve 122 is pulled with respect to the strap 112, a force is exerted on the releasable joint 124. When the force exerted is sufficient, the releasable joint 124 will break and/or release and the sleeve 122 can be removed from the strap 112. Once the sleeve 122 is removed from the strap 112, the implant 100 is in the second configuration.

In use, the implant 100 is inserted into a body of a patient while in the first configuration. In some embodiments, the implant 100 is disposed within the pelvic region of the patient. The strap 112 and the sleeve 122 are pulled through a pelvic tissue, such as the sacrospinous ligament or arcus tendineus fasciae pelvis. Once the strap 112 is positioned within the pelvic tissue, the sleeve is pulled with respect to the support member 110 in the direction shown by the arrow AA in FIG. 2 while holding the strap 112 in place. The strap 112 can be held in place by, for example, a finger, an instrument, or the pelvic tissue itself. When the sleeve is pulled, a force sufficient to break and/or release the releasable joint 124 is exerted on the releasable joint 124 such that the releasable joint 124 breaks. The sleeve 122 can then be removed from the strap 112 and the implant 100 moved into the second configuration. The strap 112 is left within the pelvic tissue to support the support member 110 of the implant 100.

In some embodiments, once the sleeve 122 is removed from the strap 112 and the strap 112 is disposed within the pelvic tissue, the strap 112 can be further adjusted such that the implant 100 adequately supports a portion of the body of the patient. In other embodiments, after the strap is disposed within the pelvic tissue, any excess portions of the strap can be removed from the strap.

Figure 3:
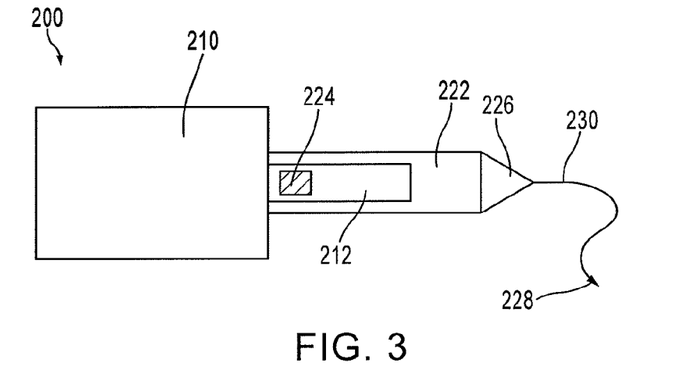
FIGS. 3 and 4 are schematic illustrations of an implant in a first configuration and a second configuration respectively, according to an embodiment.
Figure 4:
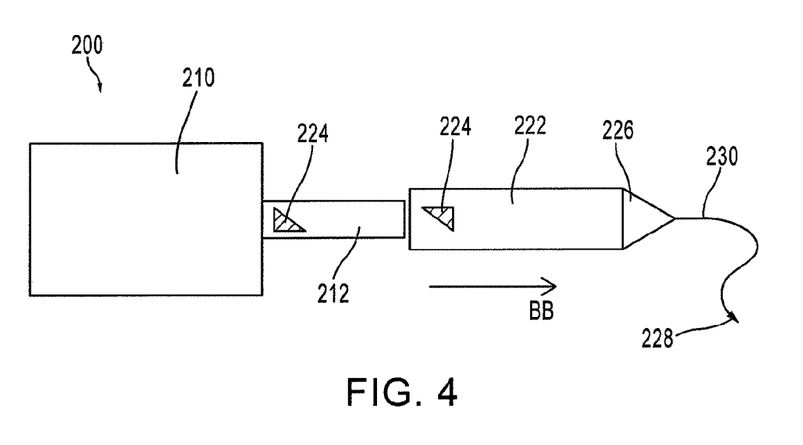

In some embodiments, an implant can include a dilator, a leader, and/or a needle attached to the sleeve to aid in inserting the strap into a tissue. For example, FIGS. 3 and 4 are schematic illustrations of an implant 200 having a dilator 226, a leader 230, and a needle 228, in a first configuration and a second configuration, respectively, according to an embodiment. The implant 200 also has a support member 210, a strap 212, and a sleeve 222 coupled to the strap 212 by a releasable joint 224. The support member 210, the strap 212, the sleeve 222 and the releasable joint 224 are similar to the support member 110, the strap 112, the sleeve 122 and the releasable joint 124, described above.

As shown in FIG. 3, a dilator 226 is coupled to the sleeve 222 and used to assist in the delivery of the implant 200 to the pelvic region. A proximal end portion (or trailing end) of a dilator 226 is coupled to the sleeve 222 by, for example, crimping, knotting, heat bonding, heat sealing, stitching, stretching, tipping or a combination thereof. In some embodiments, the sleeve 222 is formed monolithically with the dilator 226. The dilator 226 is configured to produce a passage through tissue to facilitate strap placement. Using a dilator 226 to introduce the first strap 212 into a pelvic region can help reduce handling or pulling of the implant 200 itself, thereby reducing or eliminating potential damage to the implant 200.

The dilator 226 can have a variety of different configurations. For example, the dilator 226 can be a variety of different lengths, shapes, diameters, etc. The dilator 226 can expand a passage formed by a needle 228 (as described below) during insertion through a tissue to ease the transition of the opening of the tissue to a cross-section of the sleeve 222. The dilator 226 can be flexible, semi rigid, or rigid. The dilator 226 can be curved or substantially linear. In some embodiments, the dilator 226 is tubular shaped. For example, the dilator 226 can define a lumen therethrough. The dilator 226 can also be tapered from a larger diameter at a proximal or trailing end to a smaller diameter at a distal or leading end of the dilator 226. The dilator 226 can also be color-coded. For example, when an implant having multiple straps is to be delivered to a pelvic region, dilators each having a unique color to indicate where each strap is to be placed within a pelvic region can be coupled to each strap. Such color-coding can help with the organization of the delivery process. In some embodiments, the sleeves associated with the straps can be color-coded in a similar manner as described for the dilators. In some embodiments, both the sleeves and the dilators are color-coded.

As shown in FIG. 3, a leader 230 is coupled to a distal end portion of the dilator 226 and a needle 228 is coupled to a distal end of the leader 230. In some embodiments, the leader 230 is a suture. The leader 230 can be formed, for example, with a polymer. In other embodiments, the leader is made from metal or other fiber and can be attached at one or more locations of a sleeve and/or dilator. The leader 230 is coupled to the dilator 226 and/or sleeve 222 by, for example, gluing, thermo-bonding, knotting or other methods of attachment. In some embodiments, the leader 230 is a portion of (or formed monolithically with) a leader used to couple the sleeve 222 to a strap 212.

The needle 228 can be formed with various biocompatible materials, such as, for example, stainless steel, or other surgical steel. In some embodiments, the needle 228 is used to associate the strap 212 of the implant 200 to a delivery device, such as those described in further detail herein.

A length of the leader 230 (measured from a distal end of the dilator 226) can vary. For example, in some embodiments, the length of the leader 230 is sufficiently long to be placed through a selected tissue anchoring site (after entering the pelvic region via a vaginal incision), and passed out through the vaginal incision, without requiring the dilator 226 to enter the vagina (e.g., after passing through a tissue within the pelvic region). In some embodiments, the length of the leader 230 can allow the physician to remove the needle 228 from a delivery device external to the body before a dilator 226 is pulled into the tissue or ligament. The insertion and delivery of an implant using a delivery device is described in further detail herein.

In other embodiments, rather than a leader and a needle, the dilator or sleeve can include a connector portion that can be used to associate the straps to a delivery device. For example, the dilator or sleeve can include a connector portion (not shown). In some embodiments, a loop connector is coupled to the sleeve or dilator. Such a connector or connector portion can be used to associate the dilator or sleeve to a delivery device, as described herein.

In use, the strap 212 can be pulled through a pelvic tissue using, for example, the sleeve 222 and/or the dilator 226 that is configured to dilate or expand the tissue and provide a lead-in (e.g., passageway) for the strap 212 to be pulled through the tissue. The pelvic tissue is dilated such that the strap 212 can be pulled through the tissue, but then prolapses or retracts to a smaller size to provide a frictional interaction between the tissue and the strap 212. The strap 212 can also be flexible such that even if a width of the strap 212 is greater than a width of a corresponding passage in the tissue formed by the lead-in device (e.g., dilator or sleeve), the strap 212 can flex to be pulled through the tissue, and the tissue can dilate or expand to receive the strap 212. In some embodiments, one or more straps are tapered toward their distal end, and are larger in width near the support portion, which further provides a lead-in through the tissue.

Delivery devices can be used to deliver the strap 212 of the implant 200 to and/or through a pelvic tissue, such as, for example, a levator muscle (e.g., levator ani muscle), a sacrospinous ligament, a tendineus arch of levator muscle (also referred to herein as "arcus tendineus fasciae pelvis" or "white line"), obturator muscles, an iliococcygeus muscle, and/or to other anatomical securement sites within the pelvic region of a patient. The delivery device can also be used to pass a suture end through a wall of a vagina or to pass a suture through the epithelium of a vaginal wall without passing the suture through the vaginal wall. For example, the strap 212 of the implant 200 can be deposited at selected tissue sites within the pelvic region and a portion of the implant 200 can also be coupled to a vagina of the patient, to a wall of the vagina, secured inside the vagina (e.g., within a vaginal lumen) or within the pelvic region.

The implant 200 can be delivered using a transvaginal approach using for example, any device capable of placing and/or securing the implant 200 within the pelvic region of a patient. In one embodiment, for example, a Capio® Suture Capture Device manufactured by BSC is used. An example of such a suturing device is described in U.S. Pat. No. 5,741,277, the disclosure of which is hereby incorporated by reference in its entirety. Other types of delivery devices can alternatively be used, such as, for example, the suturing device described in U.S. Patent Pub. 2004/0181243 A1 to Chu et al., entitled Re-shapeable Medical Device, the disclosure of which is hereby incorporated by reference in its entirety. In such a procedure, the implant 200 is inserted through, for example, a single vaginal incision. The incision can be, for example, through the anterior vaginal mucosa.

The strap 212 of the implant 200 can alternatively be implanted using, for example, a delivery needle, such as an Obtryx® Halo, Curve, Advantage® or Lynx® device each manufactured by BSC. An example of such devices is described in U.S. Patent Pub. No. 2005/0075660 and U.S. Patent Pub. No. 2005/0177022, the entire disclosures of which are hereby incorporated by reference in their entirety.

The implant 200 can also be configured to be associated to other delivery devices not specifically described herein. In some embodiments, the strap 212 of the implant 200 itself is configured to be associated to a delivery device. For example, a connector can be coupled directly to the strap 212 for association to a delivery device, or the strap 212 can include, for example, an opening or hole configured to associate the strap 212 to a delivery device. In some embodiments, the leader and needle can be coupled directly to a strap. In other embodiments, the straps of the implant are delivered to or through a pelvic tissue without the use of a delivery device. In such an embodiment, the needles and the straps are inserted into the a tissue by hand. In this manner, the straps are secured to the tissue.

Although the above-described embodiments describe securing a strap 222 to tissue without the use of a separate anchoring device (for example, securing with tangs of a strap), it should be understood that the implants described herein can also include anchors or other mechanical fasteners to secure one or more straps to the pelvic tissue. For example, a suture can be used to secure a strap or other portion of an implant to pelvic tissue.

In some embodiments, a portion of the support portion 210 is separately attached to a tissue within the pelvic region. Said another way, a portion of the support portion 210 can be secured by means other than the straps. For example, a suture can be threaded through the mesh support portion 210 and attached to adjacent pelvic tissue. This can provide additional support for the support portion 210.

Once the strap 212 is positioned within the pelvic tissue, the sleeve 222, the dilator 226, the leader 230 and the needle 228 can be removed from the body of the patient. This is done by pulling the sleeve with respect to the support member 210 in the direction shown by the arrow BB in FIG. 4 while holding the strap 212 in place. The strap 212 can be held in place by, for example, a finger, an instrument, or the pelvic tissue itself. When the sleeve is pulled, a force sufficient to break and/or release the releasable joint 224 is exerted on the releasable joint 224 such that the releasable joint 224 breaks. The sleeve 222 can then be removed from the strap 212 and the sleeve 222, the dilator 226, the leader 230 and the needle 228 can be removed from the body of the patient. The strap 212 is left within the pelvic tissue to support the support member 210 of the implant 200.

Figure 5:
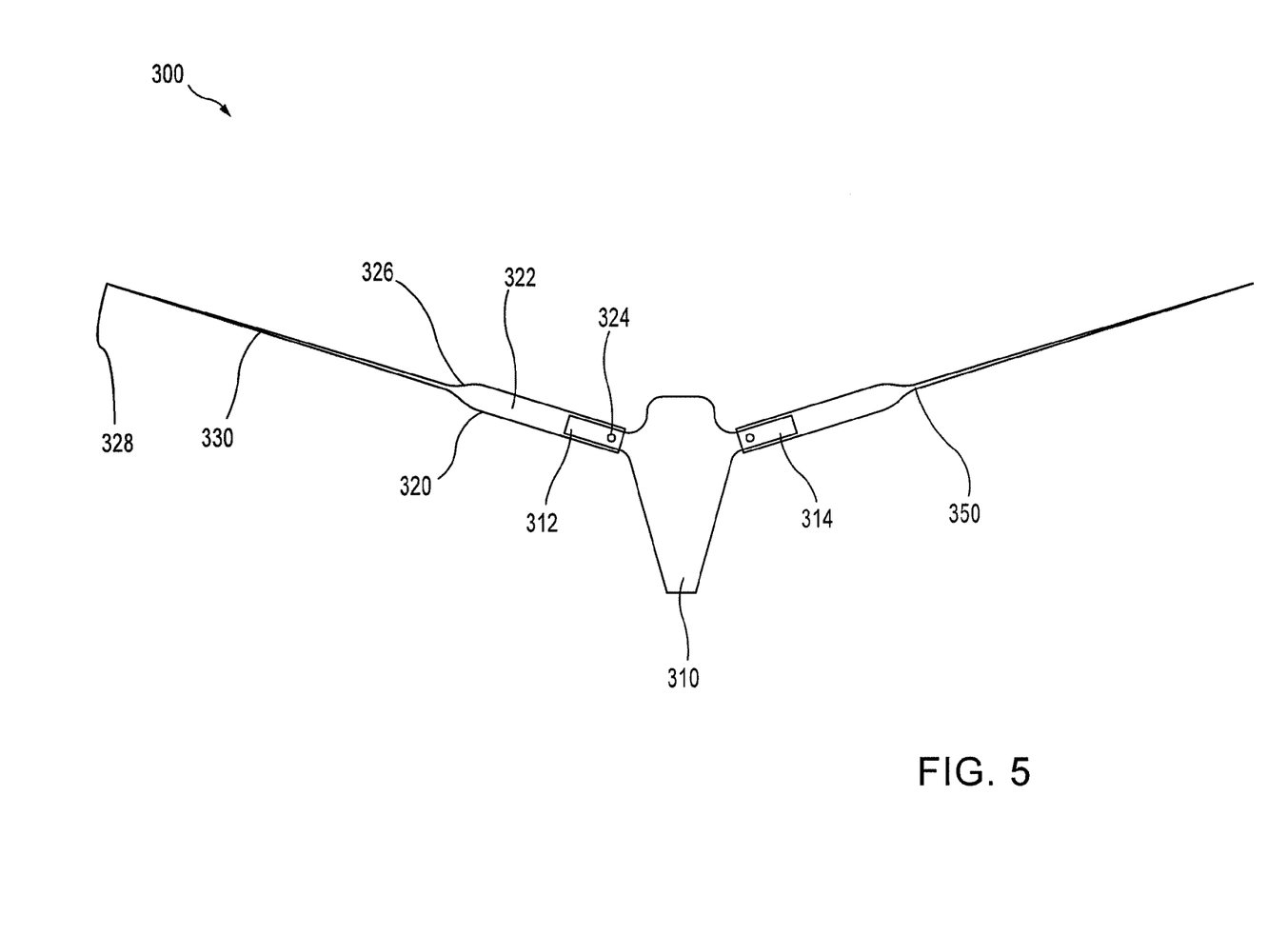
FIG. 5 is a top view of an implant, according to an embodiment.

FIG. 5 shows a top view' of an implant 300, according to an embodiment. Implant 300 includes a support portion 310, a first strap 312, a first sleeve assembly 320 coupled to the first strap 312, a second strap 314, and a second sleeve assembly 350 coupled to the second strap 314.

The support portion 310 of the implant 300 is functionally similar to the support portion 110 of the implant 100 described above. Specifically, the support portion of the implant is configured to support a portion of a pelvic floor of a patient.

The first strap 312 and the second strap 314 are also functionally similar to the strap 112 of implant 100 described above. The first strap 312 and the second strap 314 are configured to support the support portion 310 of the implant 300 when first strap 312 and the second strap 314 are disposed within a tissue of a patient.

Figure 6:
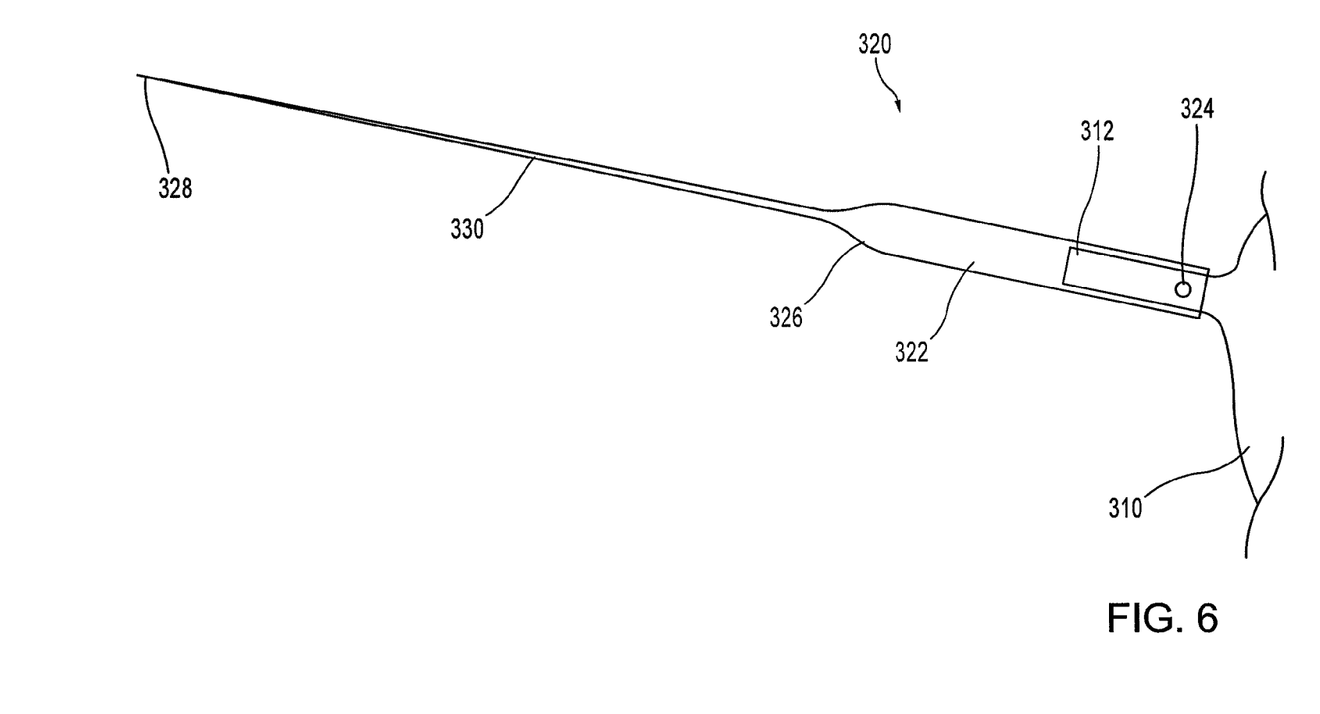
FIG. 6 is a top view of a portion of the implant of FIG. 5.

FIG. 6 shows a detailed view of the first strap 312 and the first sleeve assembly 320. The first sleeve assembly 320 includes a sleeve 322, a dilator 326, a leader 330 and a needle 328. The sleeve 322 can be made of a material such as a polymer and defines a lumen. The sleeve 322 is configured to be coupled to at least a portion of the first strap 312, such that the portion of the first strap 312 is disposed within the lumen defined by the sleeve 322. Similar to the sleeves described above, the sleeve 322 can be used during the insertion of the implant 300 into a pelvic region to prevent the first strap 312 from prematurely engaging tissue during the delivery procedure.

The sleeve 322 of the first sleeve assembly 320 is releasably coupled to the first strap 312 by a releasable joint 324. Releasable joint 324 is functionally similar to the releasable joint 124, described above. The releasable joint 324 is configured to break and/or release when a sufficient force is exerted on the releasable joint, such as, for example, about 4 lbf to 6 lbf. In this manner, the first sleeve assembly 320 can be removed from the first strap 312 when the first strap 312 is disposed within a tissue of a patient. Positioning the releasable joint 324 close to the support portion 310 minimizes the chance that the first strap 312 will stretch and/or inadvertently uncouple from the support portion 310 when the sleeve 322 of the first sleeve assembly 320 is pulled and a force is exerted on the releasable joint, as described above.

The dilator 326 is coupled to the sleeve, the leader 330 is coupled to the dilator 326, and the needle 328 is coupled to the leader 330. Similar to the dilator 226, the leader 230 and the needle 228 of the implant 200 described above, the dilator 326, the leader 330 and the needle 328 are used to help in the insertion of the implant 300 to the pelvic region of a patient.

In some embodiments, the dilator 326 is thermo bonded to the sleeve 322 of the first sleeve assembly 320.

In some embodiments, the first sleeve assembly 320 or a portion of the first sleeve assembly 320 is monolithically formed. For example, the dilator 326 and the leader 330 can be monolithically formed with the sleeve 322. In such an embodiment, the needle 328 is crimped to the leader 330. In other embodiments, the dilator, the leader, and the needle are monolithically formed with the sleeve.

The second sleeve assembly 350 is structurally and functionally similar to the first sleeve assembly 320. Additionally, the second sleeve assembly 350 is associated with the second strap 314 in a similar fashion as the first sleeve assembly 320 is associated with the first strap 312. In other embodiments, the second sleeve assembly is structurally and/or functionally different than the first sleeve assembly. For example, the length of the second sleeve assembly can be different than the length of the first sleeve assembly and/or the force needed to remove the second sleeve assembly from the second strap can be different than the force needed to remove the first sleeve assembly from the first strap.

Figure 7:
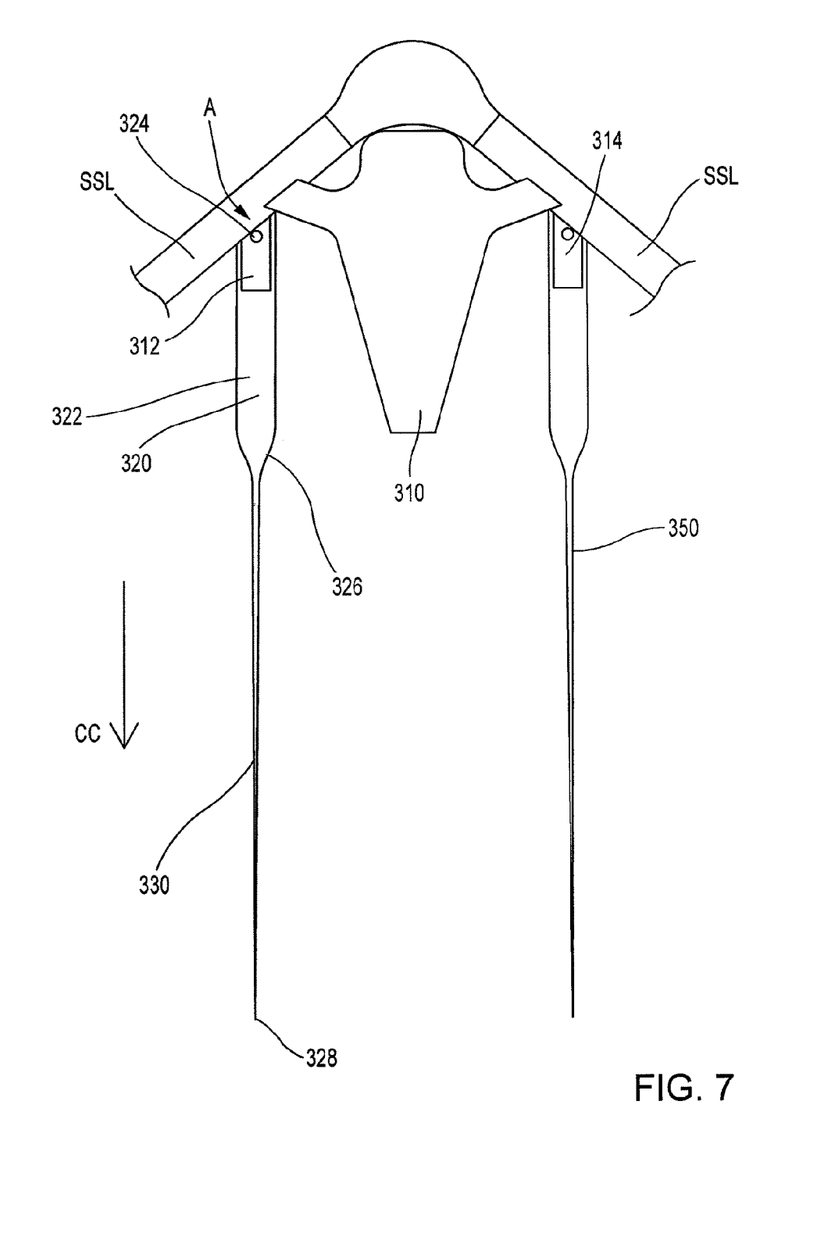
FIG. 7 is an illustration of an implant being inserted into a body of a patient, according to an embodiment.

FIG. 7 shows the implant 300 being inserted into the pelvic region of a patient. Specifically, the first strap 312 and the second strap 314 of the implant 300 are inserted into a first portion of a sacrospinous ligament SSL and a second portion of a sacrospinous ligament SSL of the patient, respectively.

The first strap 312 of the implant 300 is inserted into the first portion of the sacrospinous ligament SSL by pulling the needle 328, the leader 330, the dilator 326, and the sleeve 322 of the first sleeve assembly 320 through the sacrospinous ligament SSL. A delivery device, such as those described above, can be used to aid in inserting the first strap 312 and the first sleeve assembly 320 into the sacrospinous ligament SSL. Once the first strap 312 (still covered by the sleeve 322) is disposed within the sacrospinous ligament, the second strap 314 can be inserted into a second portion of the sacrospinous ligament SSL using the second sleeve assembly 350, as shown in FIG. 7.

Once both the first strap 312 and the second strap 314 are disposed within the sacrospinous ligament SSL in their respective positions, the first sleeve assembly 320 and the second sleeve assembly 350 can be removed from the first strap 312 and the second strap 314 respectively.

The first sleeve assembly 320 is removed from the first strap 312 by retaining the first strap 312 while pulling the first sleeve assembly 320 in a direction shown by the arrow CC in FIG. 7. The first strap 312 can be retained by placing pressure on the sacrospinous ligament SSL at a location where the first strap 312 is disposed within the sacrospinous ligament SSL between an end of the sleeve 322 of the first sleeve assembly 320 and the support member 310, such as point A in FIG. 7. This can be done by using a finger and/or other medical instrument, such as the shaft of a medical instrument and/or forceps. Alternatively, the tissue within which the first strap 312 is disposed can sufficiently retain the first strap 312. The pressure applied to point A holds the first strap 312 in place while the first sleeve assembly 320 is pulled in the direction shown by the arrow CC in FIG. 7. This causes the releasable joint 324 to break. Once the releasable joint 324 is broken, the first sleeve assembly 320 can be removed from the first strap 312. After the first sleeve assembly 320 has been removed from the first strap 312, the second sleeve assembly 350 is removed from the second strap 314 in a similar manner.

Once the first sleeve assembly 320 and the second sleeve assembly 350 are removed from the first strap 312 and the second strap 314, respectively, the first strap 312 and the second strap 314 engage the surrounding tissue and support the support portion 310 in the pelvic region of the patient.

Figure 8:
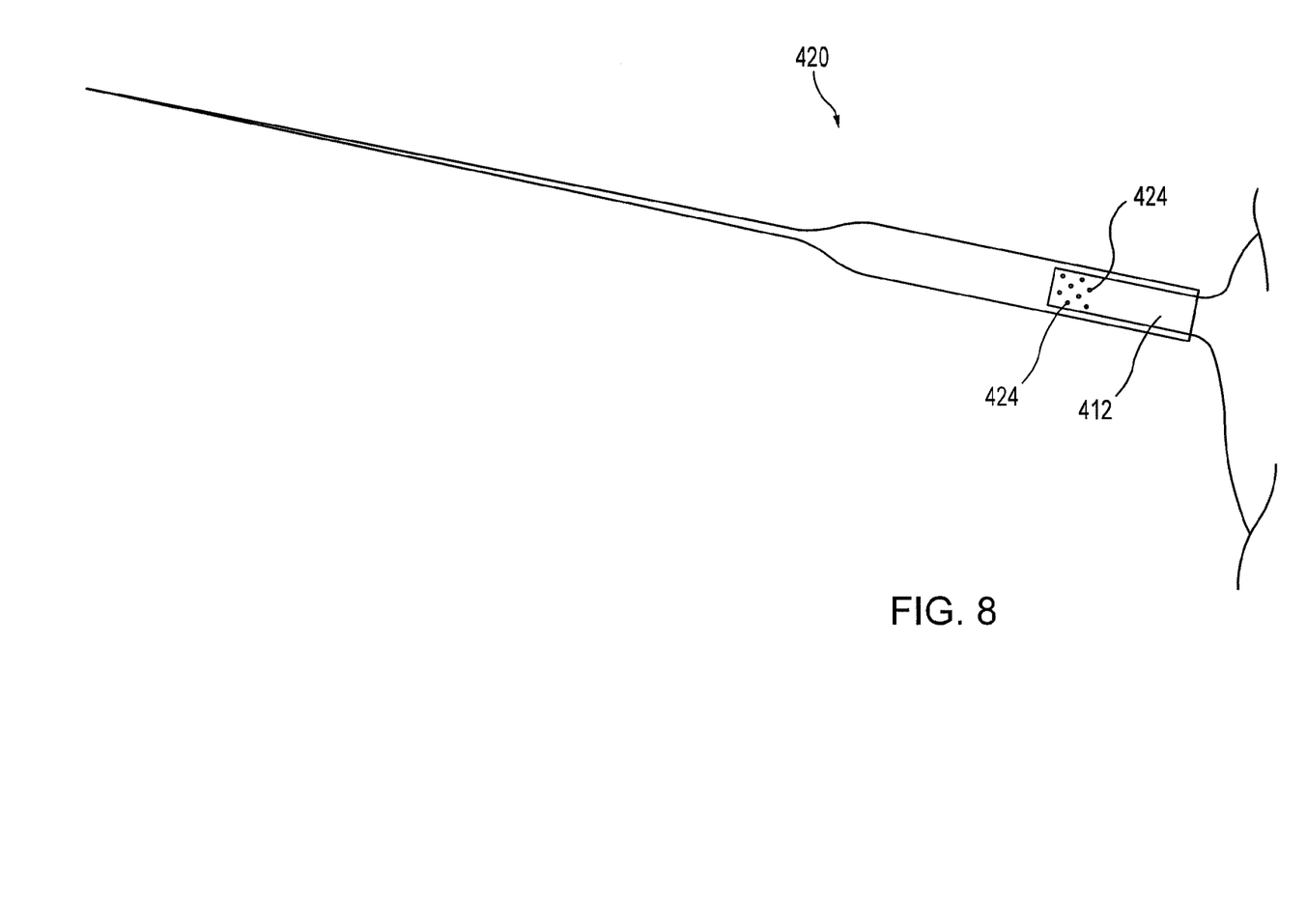
FIG. 8 is a top view of a portion of an implant, according to an embodiment.

While the first sleeve assembly 320 is coupled to the first strap 312 by a single releasable joint 324, FIG. 8 shows a sleeve assembly 420 coupled to a strap 412 by multiple releasable joints 424. This can be, for example, multiple heat welds. The multiple releasable joints 424 can be configured to break and/or release when a force of about 4 lbf to 6 lbf is applied to the releasable joints 424. Having multiple releasable joints 424 affords greater flexibility to the sleeve and can minimize damage to the strap when the releasable joints 424 are broken.

Figure 9:
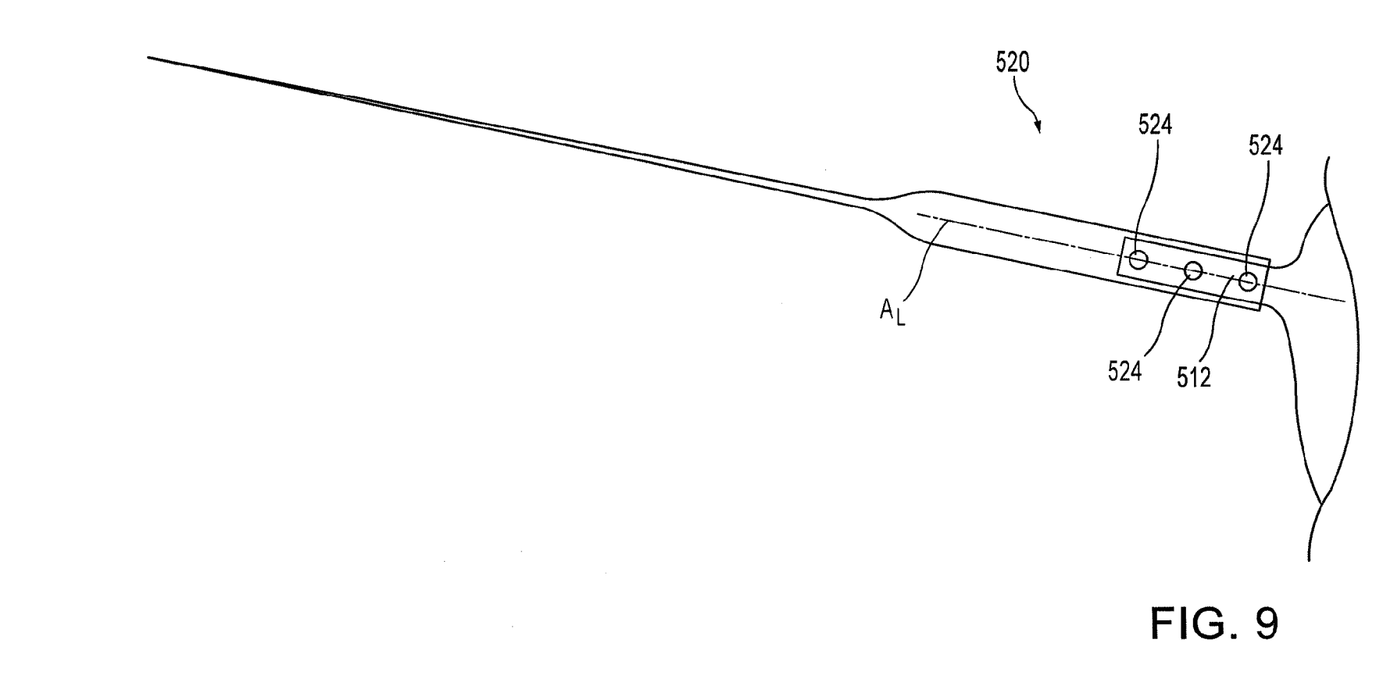
FIG. 9 is a top view of a portion of an implant, according to an embodiment.

Similarly, FIG. 9 shows a sleeve assembly 520 coupled to a strap 512 by multiple releasable joints 524. The releasable joints 524 are positioned with respect to each other along a longitudinal axis $A_L$ defined by the strap 512. Having multiple releasable joints 524 positioned along the longitudinal axis $A_L$ helps prevent the strap 512 from stretching and dislodging from the sleeve assembly 520 during handling and delivery. While shown in FIG. 9 as having three releasable joints 524, in other embodiments, any number of releasable joints can be used to couple the sleeve assembly to the strap.

Figure 10:
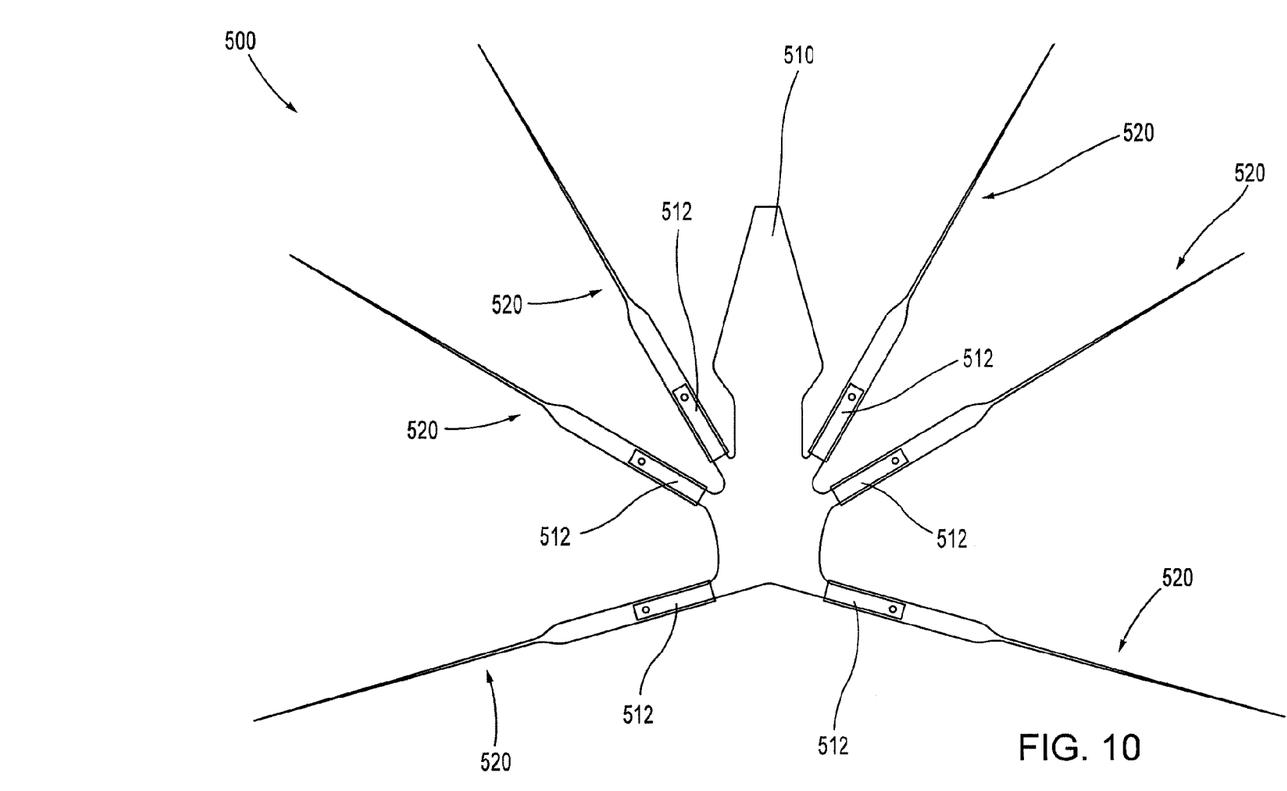
FIG. 10 is a top view of an implant, according to an embodiment.

While shown in FIG. 5 as having two straps, in other embodiments, the implant can have any number of straps. For example, FIG. 10 shows an implant 500 having a support portion 510 and six straps 512. The implant 500 also includes six sleeve assemblies 520 configured to be coupled to the six straps 512. The straps 512 and the sleeve assemblies 520 are structurally and functionally similar to the straps and sleeve assemblies described above. Having multiple straps 512 provides additional support to the support portion 510. This allows the support portion 510 to be larger and to support a larger portion of the pelvic region.

The multiple straps 512 can be inserted into a variety of tissues within the pelvic region of a patient. For example, two of the straps 512 can be placed in the sacrospinous ligament, two in the arcus tendineus fasciae pelvis and the other two in another tissue area within the pelvic region. In such an embodiment, the implant 500 can be configured to help support an anterior and/or a posterior portion of a pelvic region. In other embodiments, the number of straps and the size and shape of the support member vary depending on the application of the implant.

Figure 11:
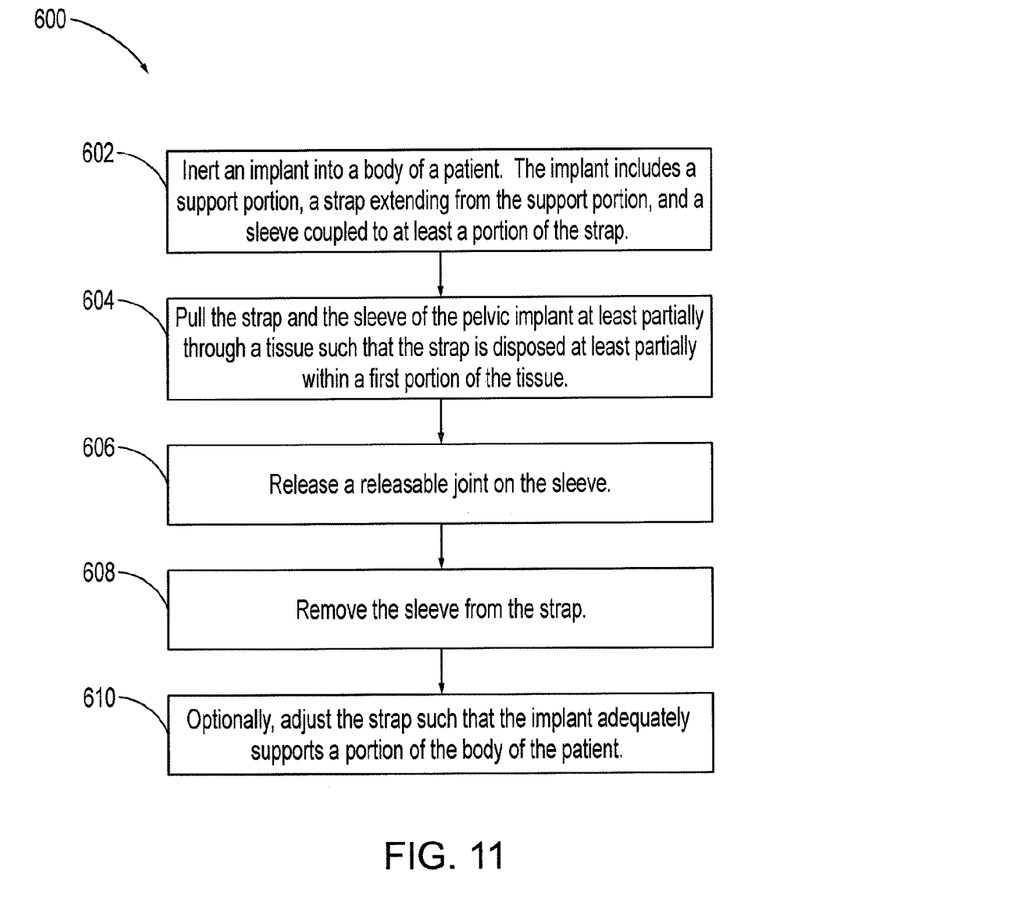
FIG. 11 is a flow chart illustrating a method of inserting an implant into a body of a patient, according to an embodiment.

FIG. 11 is a flow chart of a method 600 of inserting a pelvic implant into a body of a patient, according to an embodiment. The method 600 includes inserting an implant into a body of a patient through a vaginal incision, at 602. The implant includes a support portion, a strap extending from the support portion, and a sleeve coupled to at least a portion of the strap. The strap and the sleeve of the implant are then pulled at least partially through a tissue such that the strap is disposed at least partially within the first portion of the tissue, at 604. A releasable joint on the sleeve is then released and/or broken, at 606, and the sleeve is removed from the strap, at 608. In one embodiment, the strap is then adjusted such that the pelvic implant adequately supports a portion of the body of the patient.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, in some embodiments, the sleeve can have a reduced profile at a distal end portion, enabling it to more easily travel through the tissue during delivery. For example, the sleeve can be tapered.

In other embodiments, a support portion, a strap, and/or a sleeve are provided as separate components. For example, the support portion, the strap, and the sleeve can be provided to a user (e.g., a physician) unassembled. The user can then secure the sleeve to the strap and/or the strap to the support portion to form an implant.

Although various embodiments have been described as having particular features and/or combinations of components, other embodiments are possible having a combination of any features and/or components from any of embodiments where appropriate.

In some embodiments, an apparatus includes a support member, a strap extending from the support member and a sleeve. The support member is configured to support a portion of a body of a patient. The strap is configured to be inserted through at least a portion of a tissue of the patient. The sleeve is releasably coupled to at least a portion of the strap by a releasable joint. The sleeve is configured to be removed from the strap when at least a portion of the strap is disposed within the tissue of the patient.

In some embodiments, the releasable joint is configured to release when a force of about 4 lbf to 6 lbf is applied to the releasable joint. In some embodiments, the releasable joint includes a single weld. In other embodiments, the releasable joint includes a plurality of welds. In some embodiments, the releasable joint includes glue. In some embodiments, the releasable joint includes an interference fit. In some embodiments, the releasable joint includes a portion that can be controllably torn. In other embodiments, the releasable joint includes a fastener.

In some embodiments, the sleeve is configured to be removed from the strap in response to a force applied to the releasable joint. In some embodiments, the strap is configured to engage the tissue of the patient when the sleeve is removed from the strap. In some embodiments, the strap is configured to help retain the support member at least partially adjacent to the portion of the body of the patient when the strap is disposed within the tissue of the patient.

In some embodiments, the strap is a first strap, the sleeve is a first sleeve and the apparatus includes a second strap and a second sleeve. The second strap extends from the support member and is configured to be inserted through at least a portion of the tissue of the patient. The second sleeve is releasably coupled to at least a portion of the second strap by a releasable joint. The second sleeve is configured to be removed from the second strap when the second strap is secured to the tissue of the patient.

In some embodiments, the sleeve is directly coupled to the strap by the releasable joint. In some embodiments, the sleeve is configured to be removed from the strap by applying a force to the strap at a position along the strap between an end of the sleeve and the support member and pulling the sleeve in a direction away from the strap.

In some embodiments, an apparatus includes a sleeve, a dilator coupled to the sleeve, and a dart coupled to the dilator. The sleeve is releasably coupled to a strap of an implant by a releasable joint. The dilator is configured to dilate a tissue of a patient when the dilator is inserted through the tissue. The dart is configured to pierce the tissue of the patient when the dart is inserted through the tissue. The releasable joint is configured to be broken and the sleeve is configured to be removed from the strap of the implant when a force is applied to the strap at a position along the strap and the sleeve is pulled in a direction away from the strap.

In some embodiments, the sleeve is configured to be removed from the strap in response to a force applied to the releasable joint. In some embodiments, the releasable joint includes a single weld. In other embodiments, the releasable joint includes a plurality of welds. In some embodiments, the releasable joint includes glue. In some embodiments, the releasable joint includes an interference fit. In some embodiments, the releasable joint includes a portion that can be controllably torn. In other embodiments, the releasable joint includes a fastener.

In some embodiments, the sleeve, the dilator, and the dart are integrally formed. In some embodiments, the releasable joint is configured to release when a force of about 4 lbf to 6 lbf is applied to the releasable joint.

In some embodiments, a method includes inserting a pelvic implant into a body of a patient through a vaginal incision. The pelvic implant includes a support portion, a strap extending from the support portion, and a sleeve coupled to at least a portion of the strap. The strap and the sleeve are then pulled at least partially through a pelvic tissue such that the strap is disposed at least partially within the pelvic tissue. A releasable joint on the sleeve is then released and the sleeve removed from the strap.

In some embodiments the releasing includes applying a force to the releasable joint on the sleeve. In some embodiments, the removing includes pulling the sleeve in a direction away from the strap.

In some embodiments, the method further includes adjusting the strap such that the pelvic implant adequately supports a portion of the body of the patient. In some embodiments, the releasing includes applying a tension to the strap between an end of the sleeve and the support portion and pulling the sleeve in a direction away from the strap.

What is claimed is:

1. An apparatus comprising:
   a support member configured to support a portion of a body of a patient, the support member having a width;
   a strap extending from the support member, the strap configured to be inserted into a tissue of the patient, the strap having a first end and a second end, the strap having a width less than the width of the support member; and
   a sleeve releasably coupled to the strap, the sleeve being releasably coupled to the strap by a releasable joint, the releasable joint being disposed between a first end of the sleeve and a second end of the sleeve, the releasable joint being disposed between the first end of the strap and the second end of the strap, the sleeve configured to be removed from the strap when at least a portion of the strap is disposed within the tissue of the patient.

2. The apparatus of claim 1, wherein the releasable joint is configured to break when a force of about 4 lbf to 6 lbf is applied to the releasable joint.

3. The apparatus of claim 1, wherein the releasable joint includes a single weld.

4. The apparatus of claim 1, wherein the releasable joint includes a plurality of welds.

5. The apparatus of claim 1, wherein the releasable joint includes glue.

6. The apparatus of claim 1, wherein the releasable joint includes an interference fit.

7. The apparatus of claim 1, wherein the releasable joint includes a portion that can be controllably torn.

8. The apparatus of claim 1, wherein the releasable joint includes a fastener.

9. The apparatus of claim 1, wherein the sleeve is removed from the strap by applying a force to the releasable joint.

10. The apparatus of claim 1, wherein the strap is configured to engage the tissue of the patient when the sleeve is removed from the strap.

11. The apparatus of claim 1, wherein the strap is configured to help retain the support member at least partially adjacent to the portion of the body of the patient when the strap is disposed within the tissue of a patient.

12. The apparatus of claim 1, wherein the strap is a first strap and the sleeve is a first sleeve, the apparatus further comprising:
    a second strap extending from the support member, the second strap configured to be inserted into a tissue of the patient; and
    a second sleeve releasably coupled to at least a portion of the second strap, the second sleeve being releasably coupled to the second strap by a releasable joint, the second sleeve configured to be removed from the second strap when the second strap is secured to the tissue of the patient.

13. The apparatus of claim 1, wherein the sleeve is directly coupled to the strap by the releasable joint.

14. The apparatus of claim 1, wherein the sleeve is configured to be removed from the strap by applying a force to the strap at a position along the strap between an end of the sleeve and the support member and pulling the sleeve in a direction away from the strap.

15. An apparatus comprising:
    a support member configured to support a portion of a body of a patient, the support member having a width;
    a strap extending from the support member, the strap having an end disposed a distance from the support member, the strap having a width less than the width of the support member, the strap configured to be inserted into a tissue of the patient; and
    a sleeve releasably coupled to the strap, the sleeve being releasably coupled to the strap by a releasable joint, the sleeve having an end disposed a second distance from the support member when the sleeve is coupled to the strap, the second distance being greater than the first distance, the releasable joint disposed a third distance from the end of the strap, the sleeve configured to be removed from the strap when at least a portion of the strap is disposed within the tissue of the patient.

16. The apparatus of claim 15, wherein the releasable joint is configured to break when a force of about 4 lbf to 6 lbf is applied to the releasable joint.

17. The apparatus of claim 15, wherein the releasable joint includes a single weld disposed along a longitudinal axis of the strap.

18. The apparatus of claim 15, wherein the releasable joint includes a plurality of welds disposed along a longitudinal axis of the strap.

19. The apparatus of claim 15, wherein the releasable joint includes glue.

20. The apparatus of claim 15, wherein the releasable joint includes an interference fit.

21. The apparatus of claim 15, wherein the releasable joint includes a portion that can be controllably torn.

22. The apparatus of claim 15, wherein the releasable joint includes a fastener.

23. The apparatus of claim 15, wherein the sleeve is directly coupled to the strap by the releasable joint.

24. The apparatus of claim 15, wherein the sleeve is configured to be removed from the strap by applying a force to the strap at a position along the strap between an end of the sleeve and the support member and pulling the sleeve in a direction away from the strap.

25. An apparatus comprising:
a support member configured to support a portion of a body of a patient, the support member having a width;
a strap extending from the support member, the strap defining a longitudinal axis, the strap having a width less than the width of the support member, the strap configured to be inserted into a tissue of the patient; and
a sleeve releasably coupled to the strap, the sleeve being releasably coupled to the strap by a first releasable joint and a second releasable joint, the first releasable joint being disposed along the longitudinal axis, the second releasable joint being disposed along the longitudinal axis, the sleeve configured to be removed from the strap when at least a portion of the strap is disposed within the tissue of the patient.

26. The apparatus of claim 25, wherein the first releasable joint is configured to break when a force of about 4 lbf to 6 lbf is applied to the releasable joint.

27. The apparatus of claim 25, wherein the first releasable joint is disposed between a first end portion of the sleeve and a second end portion of the sleeve.

28. The apparatus of claim 25, wherein the first releasable joint is disposed between a first end portion of the sleeve and a second end portion of the sleeve, the first releasable joint is disposed between a first end portion and a strap and a second end portion of the strap.

* * * * *